(12) United States Patent
Turner, III

(10) Patent No.: US 7,131,444 B1
(45) Date of Patent: Nov. 7, 2006

(54) INTERNAL IMPLEMENT ALLOTROPY SEXUAL AID UTENSIL UNIVERSAL-DISK

(75) Inventor: Jacob Turner, III, 11115 Sherman Way, Apt. 203, Sun Valley, CA (US) 91352

(73) Assignee: Jacob Turner, III, Sun Valley, CA (US)

( * ) Notice: Subject to any disclaimer, the term of this patent is extended or adjusted under 35 U.S.C. 154(b) by 0 days.

(21) Appl. No.: 11/294,195

(22) Filed: Dec. 6, 2005

(51) Int. Cl.
*A61F 5/37* (2006.01)
(52) U.S. Cl. ...................... 128/883; 128/884
(58) Field of Classification Search ............... 128/830, 128/846, 883, 884, 840, 844
See application file for complete search history.

(56) References Cited

U.S. PATENT DOCUMENTS

| | | | | |
|---|---|---|---|---|
| 4,167,183 A | * | 9/1979 | Barlow | 128/884 |
| 4,237,876 A | * | 12/1980 | Rumph et al. | 128/884 |
| 5,769,090 A | * | 6/1998 | Brown | 128/883 |
| 6,250,304 B1 | * | 6/2001 | Turner, III | 128/883 |
| 6,935,343 B1 | * | 8/2005 | Turner, III | 128/883 |

\* cited by examiner

*Primary Examiner*—Michael A. Brown
(74) *Attorney, Agent, or Firm*—Jacob Turner, III

(57) ABSTRACT

The invention is made of a soft but firm FDA approved polymer/thermoplastic medical grade. Containing within its structure different wall thickness and shape of material resilient hollow receptacle tip, sharp circular projectile disk and dimensional hole in center, circular elongated tubular one piece with external raised ribs, string for removal. It can be lubricated in the manner of a condom. The resilient hollow receptacle tip surrounds a sharp circular projectile disk and dimensional hole in the center of the source of the sharp circular projectile disk which has a specimen cavity behind the dimensional center hole for collecting specimens from a penis upon contact in attempting to penetrate the vagina. This invention is inserted into the vagina of a female wearing it in the same way as a tampon length wise and pushing it into the vaginal cavity. Upon placement in the vagina, the invention blocks the entrance to the vagina, and exposes a resilient hollow receptacle tip covering a sharp circular projectile disk with a dimensional center hole covering the specimen cavity. The sharp projectiles will inflict a sharp non-lethal pain to head of the penis attempting to penetrate the vagina, and the dimensional center hole is designed to collect specimens when the head of the penis makes contact with the sharp circular projectile disk. The invention is disposable.

4 Claims, 4 Drawing Sheets

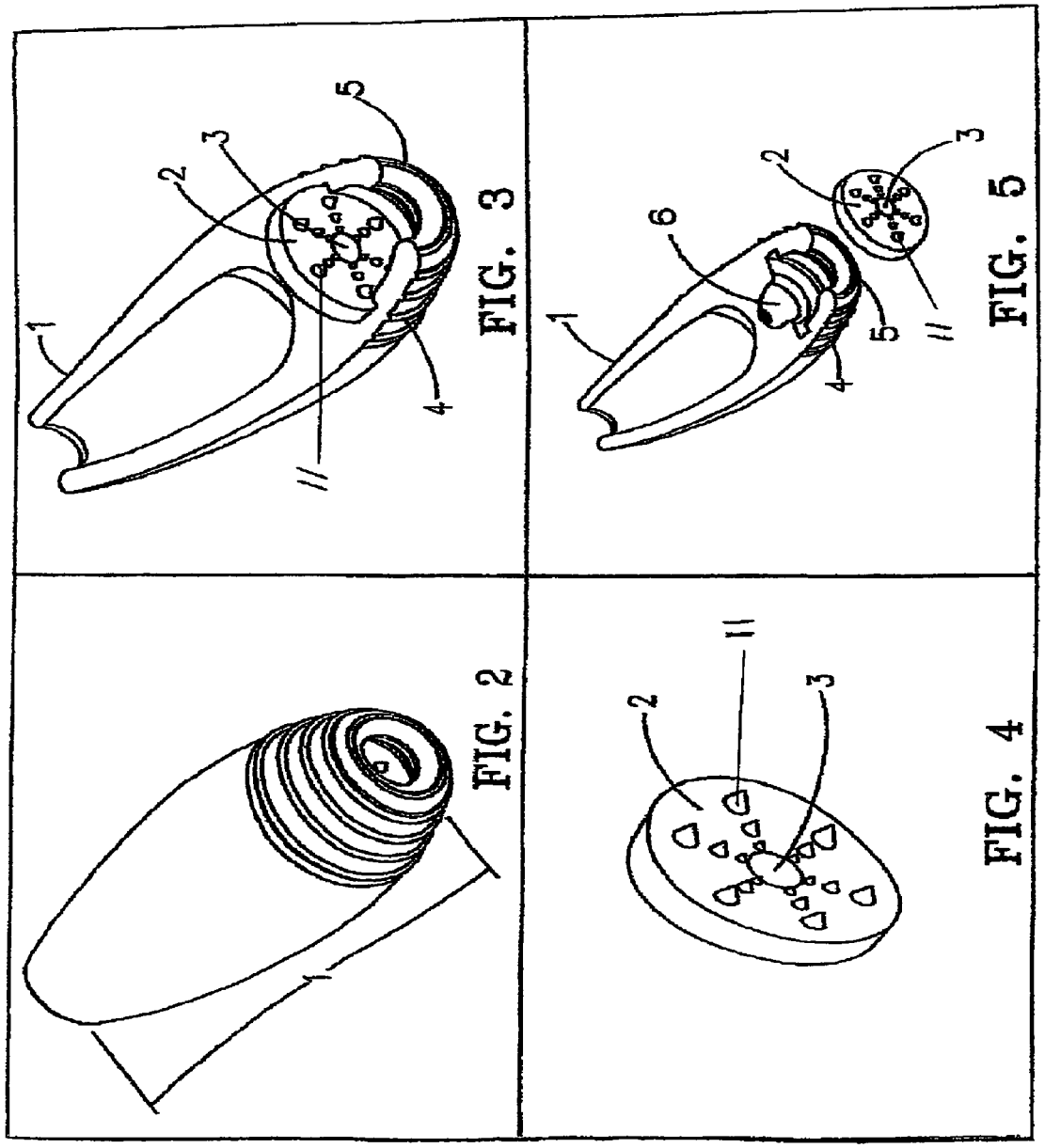

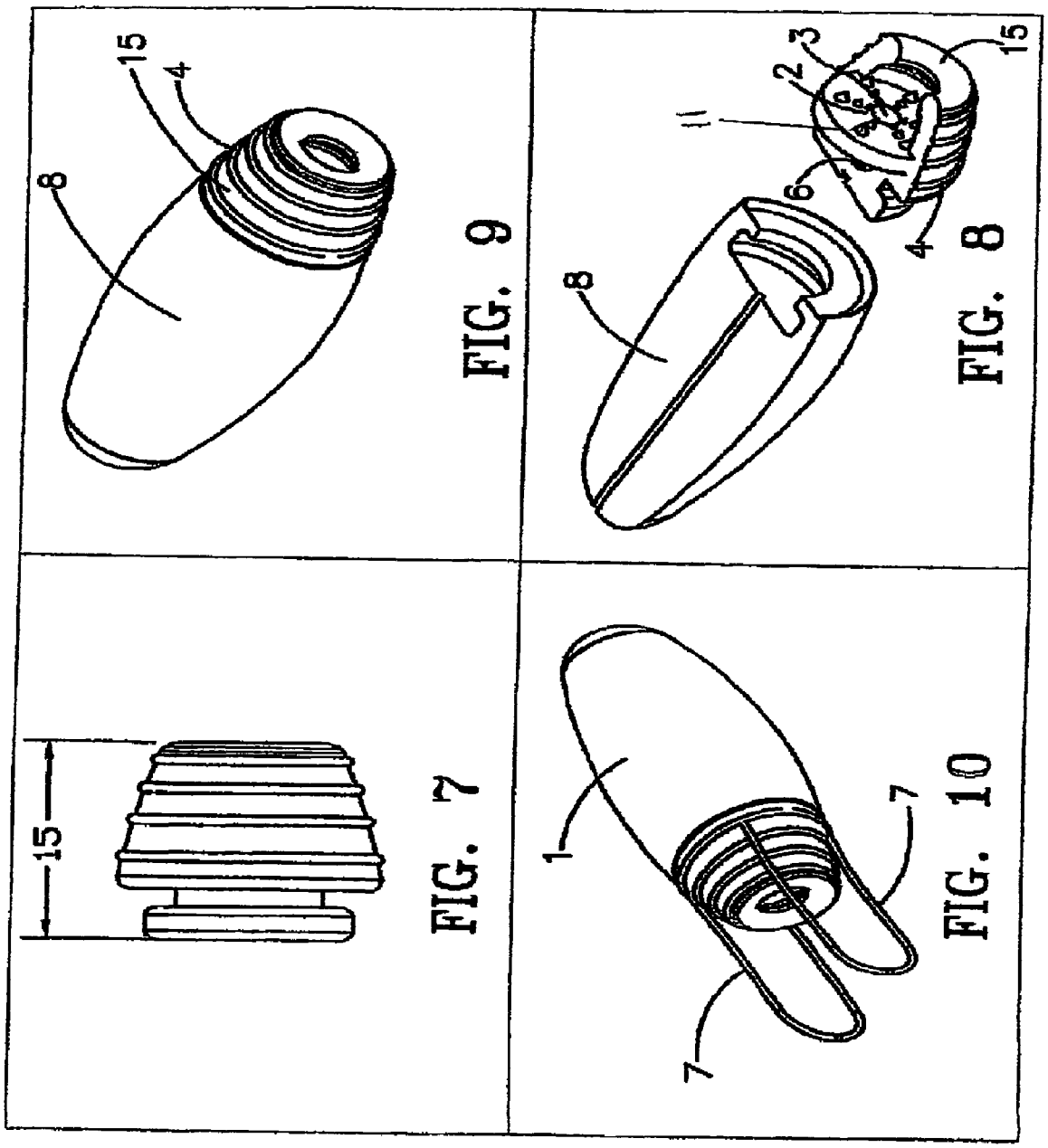

INTERNAL IMPLEMENT ALLOTROPY SEXUAL AID UTENSIL UNIVERSAL-DISK

BACKGROUND OF INVENTION

BRIEF SUMMARY

This type of invention creates a blockage device inserted into the woman's vagina and causes a sharp intense non-lethal pain to the head of the male penis, and has a sharp circular projectile disk with dimensional center hole that works by capillary attraction to collect bodily fluids into a specimen cavity, at the point of contact with the would be rapist penis. These collected samples can be used to identify the potential rapist. The modification in design is obvious. The invention is made to prevent unwanted penal penetration, and to give a non-lethal pain if forced vagina penetration is attempted, and to collect bodily fluids from the head of the would be rapist penis in a specimen cavity within the circular elongated tubular one piece embodiment. It is an intra-vaginal anti-rape invention which is made of two medically approved FDA polymer thermoplastic material. It's structure consist of a one piece circular elongated tubular embodiment with therein resilient hollow tip, which covers a sharp circular projectile disk with dimensional center hole covering a specimen cavity that works by capillary attraction to collect bodily fluids at the point of contact with the would be rapist penis. The circular elongated tubular body can be substituted for an conventional tampon depending upon the female using the invention. The purpose of the invention is to create a vaginal blocker internally that hinders penetration, and that is capable of collecting a specimen from a rape suspect with a one piece long member therein with a sharp circular projectile disk with dimensional center hole covering a specimen cavity for collecting body fluids at the point of contact by the rapist penis, and is enclosed within the resilient hollow tip with external raised an elongated ribs and this member is disposable. This invention is made to be worn by women of all ages. Size adjustments can be made according to each individual woman wearing this invention. Men considering rape, after this invention becomes known, will hopefully not attempt it, with the dread that any women could be wearing this invention and since this invention is capable of collecting a specimen that can be used to identify the rapist. The current modifications were deemed necessary in order to fully and effectively create a new standard for internal personal prevention worn in the female vagina. This current Utility patent application for Internal Allotropy Implement Sexual Aid Utensil Universal-DISK is a new design modification related to U.S. Pat. No. 6,250,304 B1, and U.S. Pat. No. 6,935,343 B1, which is herein incorporated as references.

Herein are the modifications submitted in this new Utility Patent Application. The function of this contrivance is the same in purpose, making an improved internal personal prevention device that is inserted in the female's vagina. This one piece circular elongated tubular embodiment which will hinder penis penetration has a sharp circular projectile disk with, dimensional center hole covering a specimen cavity within the embodiment to collect bodily fluids from the tip of a penis making un-wanted contact with the surface based on capillary attraction. In the previous Utility patent numbers U.S. Pat. No. 6,250,304 B1, and U.S. Pat. No. 6,935,343 B1. The four part plastic utility consisting of two receptacles, and six projectiles. The new, and embodiment as seen in the drawings in FIGS. 1–10. Improvements include using a one piece circular elongated tubular embodiment, using a sharp circular disk with multiple sharp projectiles, creating dimensional center hole, and specimen cavity for collecting bodily fluids, within a one piece embodiment and adding external raised an elongated ribs, and string for extraction. It is made of two medical FDA approved polymers material for assembly and it is disposable.

BRIEF DESCRIPTION OF THE DRAWINGS

FIG. 2. shows side view of invention internal implement allotropy sexual aid utensil Universal-DISK.

FIG. 3. shows side view of internal implement allotropy sexual aid utensil Universal-DISK with raised ribbed along the exterior of resilient tip therein is found the sharp circulars projectile disk with dimensional center hole.

FIG. 4. shows the side view of sharp circular projectile disk with dimensional center hole.

FIG. 5. shows side view of invention internal implement allotropy sexual aid utensil Universal-Disk with specimen cavity with external raised ribs along the exterior of resilient tip in addition the sharp circular projectile disk with dimensional center hole.

FIG. 7. shows side view of short resilient tip with external raised ribs.

FIG. 8. shows side view of conventional tampon un-attached to short resilient tip. therein on the exterior are raised ribs enclosed is the sharp circular projectile disk with dimensional center hole covering specimen cavity.

FIG. 9. shows side view of short assembled invention with conventional tampon attached to hallow resilient tip with external raised ribs.

FIG. 10 shows string internal implement allotropy sexual aid utensil universal-DISK.

DETAIL DESCRIPTION

Figure 1:
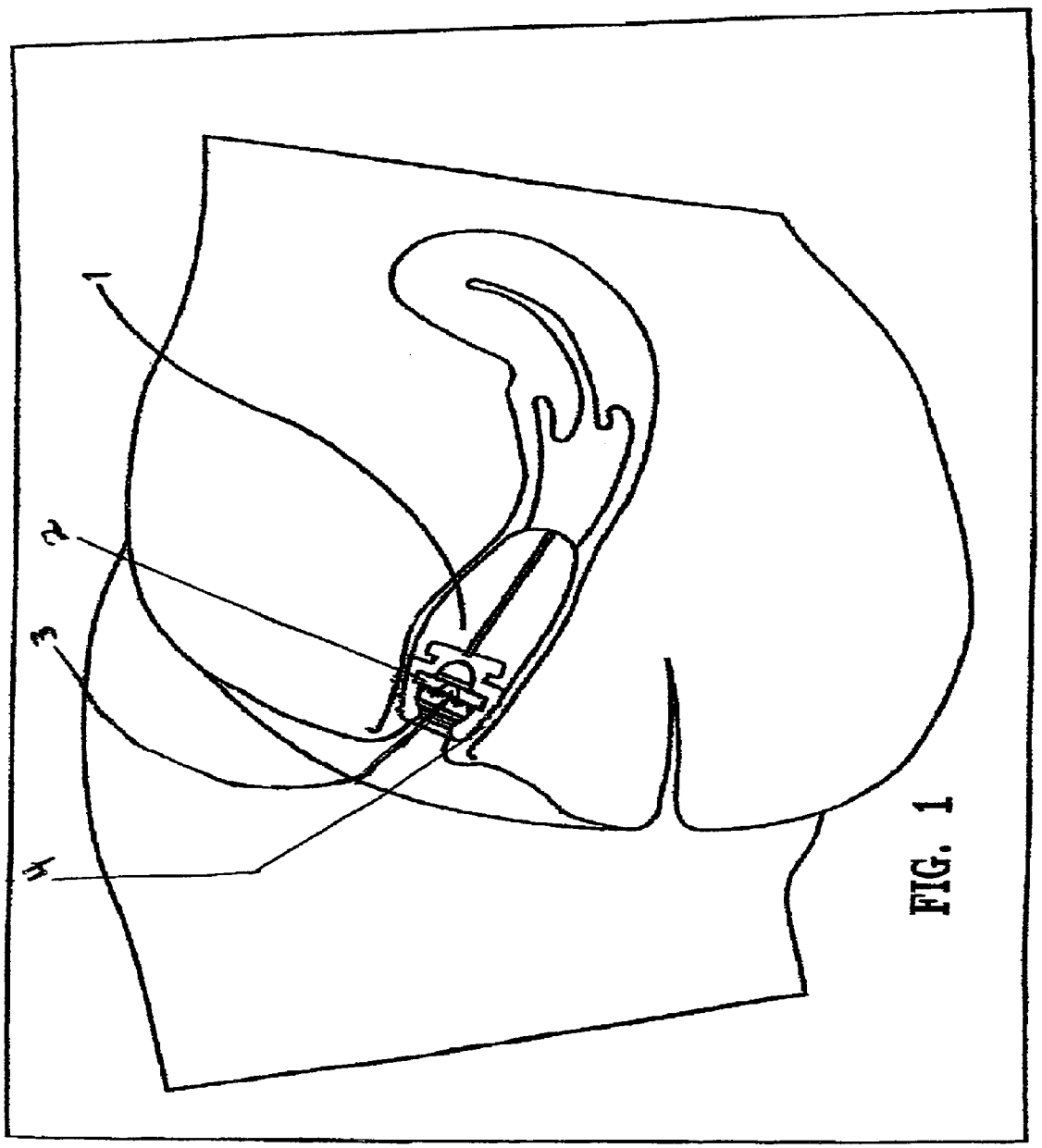
FIG. 1. shows a side view of the woman's anatomy wearing the invention. Entrance to vagina invention "internal implement allotropy sexual aid utensil Universal-DISK" inside wall of vaginal cavity.
Figure 6:
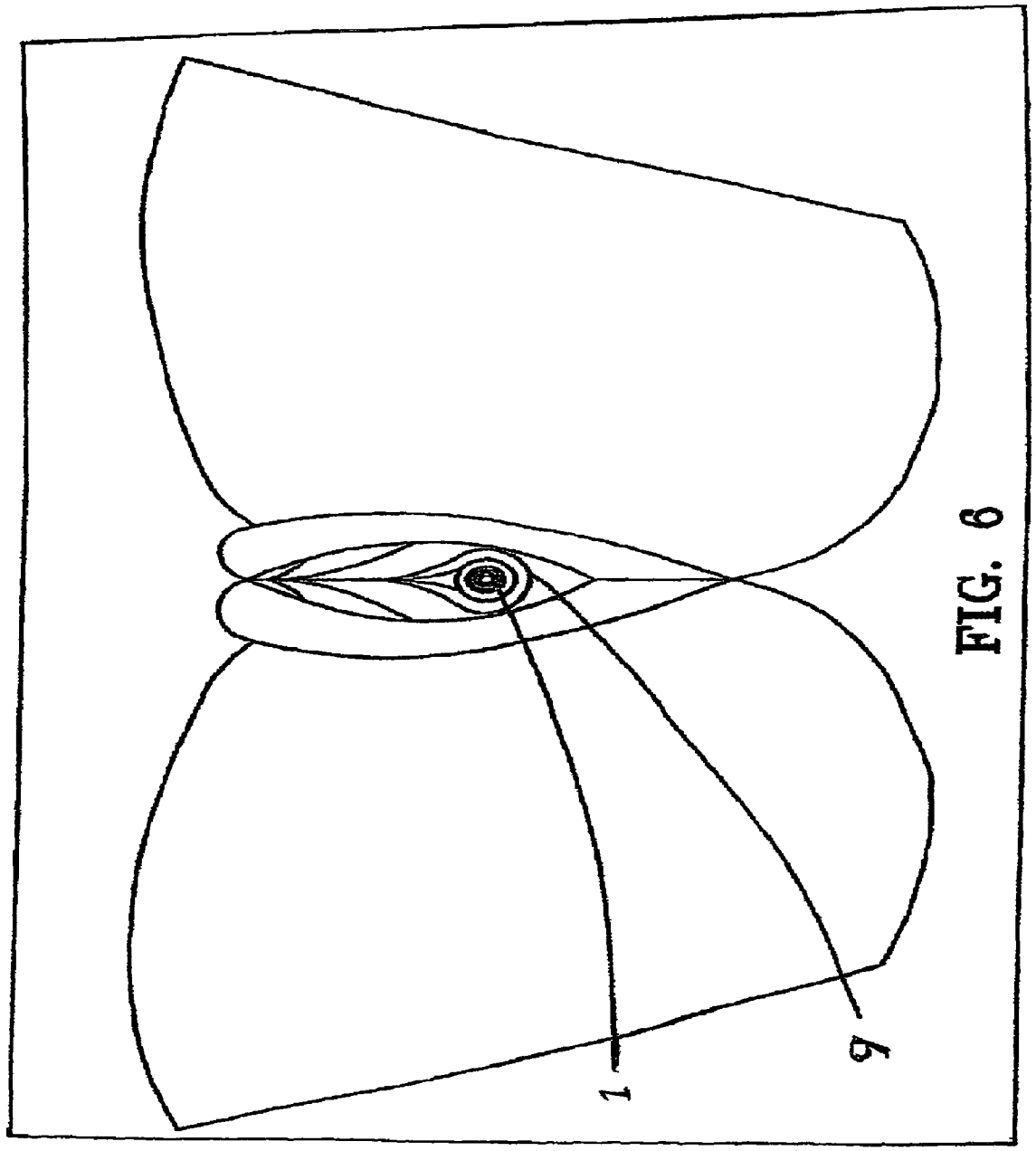
FIG. 6. shows frontal view of woman's anatomy with invention inserted in vagina. Entrance to vagina invention blocking the entrance of the vagina.

The subject matter which we refer to as the invention. Internal Implement Allotropy Sexual Aid Utensil Universal-DISK is a one piece circular tubular elongated embodiment with a sharp circular projectile disk and dimensional center hole, with a specimen cavity in one embodiment, and has surface external raised and elongated ribs. The device is made of two medically FDA approved polymer thermoplastic, which is a soft and firm material. The invention is inserted into a females vagina with the resilient hollow tip, facing the outer open end of the vaginal, containing within it's circumference a sharp circular projectile disk with dimensional center hole covering a specimen cavity. When positioned correctly points toward the outer open end of the vagina. The one piece circular tubular elongated embodiment has a resilient hollow tip at one open end, that covers the sharp circular projectile disk with dimensional center hole, this dimensional center hole covers a specimen cavity. This internal implement allotropy sexual aid utensil Universal-DISK is made of a one piece circular tubular elongated embodiment which is a secure hollow embodiment that secures the invention inside the female's vagina. The invention is made of two medically FDA approved polymer thermoplastic, and is soft and firm. The invention inserted into the vagina forms a internal preventative blocker against penal penetration. If penal penetration is attempted the resilient hollow tip, will recoil exposing the sharp circular projectile disk, and the dimensional center hole, which will prick the head of the penis giving a sharp intense non-lethal pain which will binder vagina penetration. The dimensional center hole is designed to work on the principle of capillary attraction gathering a specimen sample also when the head of the penis makes contact with the circular sharp projectile disk. When a woman is raped the penis of the rapist enters the vagina by force. With this invention it blocks the entrance of the vagina, and will collect a specimen from the head of the penis and will deliver a non-lethal sharp pain and penetration will be stopped. Once the rapist penis makes contact with the sharp circular projectile disk, the pain will distract his attention, thus giving the woman an opportunity to regain some type of advantage against the rapist. With the collected specimen the rapist can be identified. This invention is made to be worn by women of all ages. This invention will be made in different sizes to fit according to a woman's anatomy. It is disposable. It is sterilized according to medical specifications. It can be worn with a conventional tampon or without. It is recommended to wear this device 6 to 8 house, but the time can be more clearly defined by a Physician. It should be removed after 6 to 8 hours. This product will carry a warning label on all packaging stating that this device may case bodily injury to any male's penis forcing vagina penetration while this device is inserted inside the vagina. This invention will definitely give every woman a viable option to use as an internal prevention against RAPE. The Internal Implement allotropy sexual aid utensil Universal-DISK includes a one piece elongated circular tubular member 1 personal prevention device worn in the female vagina. In FIG. 1, an internal implement allotropy sexual aid utensil Universal-DISK is shown therein a circular elongated tubular member having a resilient tip 5, a sharp circular projectile disk 2 with a dimensional center hole 3, and having external raised ribs 4 on the outside of tubular member for removing the tubular member. In FIG. 2, a frontal view of the elongated tubular member 1 is shown. In FIG. 3 a cross section view of the elongated tubular member 1, an open proximal end forming a resilient tip 5 the external raised ribs 4 extend along outer surface of the elongated tubular member, and up to resilient tip. The disk 2 is configured to fit within the elongated tubular member 1. The disk 2 having a dimensional center hole 3 and sharp projectiles 11 extended from a sure of the disk. In FIG. 4 the circular projectile disk 2 with the dimensional center hole 3 is shown. In FIG. 5 cross section view of circular elongated tubular member 1 showing the resilient tip 5 the external raised ribs 4 extend along out surface of elongated tubular member and up to the resilient tip. Within the elongated tubular member is a configuration of a specimen cavity 6 currently shown outside the tubular member is the sharp circular projectile disk 2 with a dimensional center hole 3. In FIG. 6 frontal view of internal implement allotropy sexual aid utensil Universal-DISK 1 inserted in the female vagina 9. FIG. 7, shows a side view of a short member resilient tip 15. FIG. 8, shows a side view with a conventional tampon 8 therein un-attached to the short member resilient tip 15 with raised ribs on exterior 4 therein the sharp circular projectile disk 2 with dimensional center hole 3 covering specimen cavity 6. FIG. 9 shows side view of short member resilient tipi 5 with external raised ribs 4 attached to a conventional tampon 8. The Internal implement allotropy sexual aid utensil Universal-DISK is made with two FDA medically approved polymers, and is disposable. FIG. 10 shows string 7 optional way to remove invention. String 7 in FIG. 10 is disclosed from U.S. Pat. No. 6,250,304 B1, and U.S. Pat. No. 6,935,343 B1 incorporated into this Utility Patent by references.

We claim:

1. An anti-rape device comprising a hollow tubular having a resilient tip, a short resilient member inserted into the resilient tip, said short resilient member having a plurality of ribs extend around it circumference, a disc located inside of said hollow tubular member, said disc having a plurality of sharp projectiles extending from one side, said disc having a centrally located hole therein, said centrally located hole being adapted to allow semen to pass into a cavity located in said hollow tubular member behind said disc.

2. The anti-rape device of claim 1, comprising a string attached to said hollow tubular member to assist in removing the device from the vagina.

3. The anti-rape device of claim 1, comprising a polymer.

4. The anti-rape device of claim 3, comprising tampon attached to said short resilient member.

* * * * *